United States Patent [19]

Abramczyk et al.

[11] Patent Number: 4,785,243

[45] Date of Patent: Nov. 15, 1988

[54] ELECTRONICALLY SCANNED EDDY CURRENT FLAW INSPECTION

[75] Inventors: Richard F. Abramczyk, Brunswick; Steven J. Aron, Jr., Parma; Richard M. Harris, Medina; James M. Toth, Lyndhurst, all of Ohio

[73] Assignee: LTV Steel Company, Cleveland, Ohio

[21] Appl. No.: 8,572

[22] Filed: Jan. 29, 1987

[51] Int. Cl.[4] ............................................. G01N 27/90
[52] U.S. Cl. .................................... 324/232; 324/241; 324/242; 324/262
[58] Field of Search ........ 324/232, 233, 235, 239–243, 324/262

[56] References Cited

U.S. PATENT DOCUMENTS

| | | | |
|---|---|---|---|
| 2,124,579 | 7/1938 | Knerr et al. | |
| 2,467,306 | 4/1949 | Habig | 324/242 |
| 2,610,230 | 9/1952 | Wiegand | |
| 2,938,163 | 5/1960 | Roffman et al. | |
| 3,617,874 | 11/1971 | Forster | 324/241 |
| 3,875,502 | 4/1975 | Neumaier | 324/241 |
| 3,944,911 | 3/1976 | Tornblom | 324/242 |
| 4,087,749 | 5/1978 | McCormack | 324/235 X |
| 4,101,832 | 7/1978 | Baker et al. | 324/227 |
| 4,107,605 | 8/1978 | Hudgell | 324/220 |
| 4,288,747 | 9/1981 | Kawabata et al. | 324/243 |
| 4,303,885 | 12/1981 | Davis et al. | 324/237 |
| 4,379,261 | 4/1983 | Lakin | 324/232 X |
| 4,651,093 | 3/1987 | Detriche et al. | 324/232 |
| 4,742,298 | 5/1988 | Ando et al. | 324/242 X |

FOREIGN PATENT DOCUMENTS

| | | | |
|---|---|---|---|
| 0603890 | 4/1978 | U.S.S.R. | 324/232 |
| 2092799 | 8/1982 | United Kingdom | 324/232 |

*Primary Examiner*—Gerard R. Strecker
*Attorney, Agent, or Firm*—Watts, Hoffmann, Fisher & Heinke

[57] ABSTRACT

Method and apparatus for performing eddy current flaw inspection on workpiece material such as steel bar stock. A drive mechanism propels a workpiece longitudinally along a workpiece path. An array of electromagnetic transmitter coils is disposed about the workpiece path. An electromagnetic source energizes the transmitter coils under control of multiplexing circuitry. The multiplexing circuitry and source actuate respective transmitter coils in a predetermined iterative sequence. The sequential actuation induces eddy currents in the workpiece at a succession of locations extending iteratively about the workpiece circumference. Circuitry coupled to multiple, differentially wound sensing coils detects variations in eddy current produced in the workpiece and utilizes these detected variations to produce flaw indicating signals.

7 Claims, 6 Drawing Sheets

ELECTRONICALLY SCANNED EDDY CURRENT FLAW INSPECTION

DESCRIPTION

1. Technical Field

The present invention relates to an eddy current inspector for inspecting flaws along the surface of an elongated workpiece such as a steel bar and a method of conducting such inspections.

2. Background Art

In typical manufacture of steel bars and rods a billet is heated to a temperature of approximately 2300°-2400° F. and rolled into a bar shape. The rolling process produces a shape which is gradually rounded as it passes through rolling stages. The rolling process also causes significant elongation. By way of example, a 5" square cross-section billet can be rolled into a round steel bar approximately ⅜" in diameter and hundreds of feet long. The steel bar is then cut into pieces of a desired length.

In the production of steel products it is desirable to detect manufacturing flaws as soon as possible so that remedial steps can then be taken to eliminate the cause of the flaws. Once flawed product is identified it is typically repaired or rejected.

In bar manufacture for example, various inspection steps are performed on the billet prior to rolling. These inspection steps are intended to detect the presence of flaws in the billet which would produce flaws in the resulting bar product. Once the billet flaws are detected they are removed by scarfing or other procedures.

Further inspection steps are performed after bars are formed because during the rolling of the billet, other defects may be introduced. For example, a piece of foreign matter may be adhered to a bar forming roll and introduce repetitive defects in the steel as rolling occurs. As another example, if the rolls become misshaped, they can generate severe irregularities in the steel bar which on subsequent rolling may become folded over to form elongated grooves or flaws along the bar.

If finished steel bars contain flaws of less than a certain severity, the bars may be sold for their intended purpose. While inspection permits bars to be graded accoding to flaw severity so that poor quality bars can be sold as such, there are still occasions when bars are scrapped and reprocessed. Accordingly, as with earlier steps in the production process, when bar stock is being formed, it is desirable to detect the presence of flaws and determine their causes as soon as possible so corrective steps can be taken.

Procedures for detecting the presence of flaws before a product cools are known. U.S. Pat. No. 4,024,470 to Vild et al entitled "Eddy Current Detector for Hot Test Pieces Having Cooling Fluid and Purge Features" discloses apparatus where a combination of a heat shield and a fluid coolant protects detectors from the heat of a hot workpiece U.S. Pat. No. 4,101,832 to Baker et al. discloses flaw detection apparatus with a plurality of pick-up arms mounted around a workpiece path. A plurality of sensing coils are carried by the pick-up arms. The arms are pivotally mounted so the transmitter and sensing coils may be moved into proximity or away from to a workpiece path of travel.

Patents that disclose control circuitry and apparatus to classify and mark the position of defects in steel bars are U.S. Pat. Nos. 3,688,186 to Judd et al and 3,263,809 to Mandula et al as well as the '470 patent to Vild et al. An improved marking process is disclosed in recently issued U.S. Pat. No. 4,365,198 to Toth. U.S. Pat. No. 4,355,281 to Toth et al discloses an eddy current test arrangement having two detection coils spaced along a workpiece path so that as the workpiece is rotated and translated past the coils flaws are detected. The disclosures of these six patents are incorporated herein by reference.

In a typical eddy current tester, an excitation coil is placed in proximity to a electrically conductive workpiece under test. The coil is energized with an electric signal to create magnetic fields that induce eddy currents in the workpiece. A flaw in the workpiece alters the eddy current flow and this alteration can be sensed in a test coil and detected by monitoring current induced in the test coil. Prior eddy current testers for relatively deep flaws each typically included both an excitation or energization coil to set up the eddy currents in workpieces and a separate detector coil which is used in monitoring eddy currents.

Proposals have been made to modify the functioning of these prior eddy current testers. These proposals concern strengthening or enhancing a magnetic field in time varying locations around the surface of a product under test. The enhanced magnetic field produces a stronger response in the test equipment monitoring the eddy currents. These prior proposals include either a shield to selectively transmit a magnetic field to the surface of the product or, in the alternative, a rotatable magnetic field producing element moved in relation to the product. The prior art proposals for strengthening or enhancing magnetic fields about a workpiece circumference each include a mechanical structure that rotates about a workpiece.

U.S. Pat. No. 2,124,579 to Knerr et al. discloses a prior art eddy current test system. FIG. 14 of this patent show a segmented detection coil for selectively obtaining eddy current signal readings from a portion of a sensing coil. There is no suggestion in this patent, however, of selectively enhancing an excitation region of a workpiece by varying an eddy current inducing field.

DISCLOSURE OF THE INVENTION

In accordance with the invention, a scanning magnetic field is generated electronically. Electronic scanning is less susceptible to component failure and is easier to adjust than the mechanical systems of the prior art.

An eddy current flaw inspection system constructed in accordance with the invention includes a drive mechanism for propelling an elongated workpiece along a workpiece travel path. An array of transmitter coils are distributed about the workpiece is an arc. These transmitter coils are coupled to excitation circuitry that selectively energizes the coils in a sequence along the arc to induce eddy currents in the workpiece. A detection circuit senses variations in eddy currents induced in a workpiece surface during transmitter coil energization. An output from the detection circuit may be used to both identify and categorize defects in the workpiece.

Electronic exitation of the transmitter coils proceeds in an ordered sequence which can be controlled by excitation circuits to produce a rotating magnetic field. Different energization sequences can be achieved by adjusting control parameters of the energization circuits.

In the preferred construction, a number of transmitting-sensor coil sets are provided. Each set is wound on a cylindrical bobbin or support. Each bobbin has an axially spaced pair of axially aligned grooves. The coils of a bobbin's associated set are respectively wound in the grooves in axially aligned relationship.

In this embodiment, six bobbins, each supporting a set of transmitting-sensor coils, are oriented with their axes in a common plane perpendicular to a workpiece path of travel. Six additional bobbins are offset a short distance along the travel path of the workpiece in a second plane. The axes of the bobbins are radial of the axis of the travel path and the bobbins are uniformly spaced circumferentially of the path.

The bobbin grooves are preferably formed near the bobbin end closest to the travel path. The sensor coil of each bobbin is in the groove nearest to the path of travel such that the sensor coils form a ring concentric of the workpiece travel path and the transmitter or exitation coils are in a second ring which is concentric of and surrounds the sensor coil ring.

In operation the eddy current inducing magnetic field is electrically caused to orbit the workpiece path. This is preferably accomplished by sequentially energizing adjacent pairs of transmitter coils. The sensing coils are series connected. Thus, output signals caused by a given flaw will represent summations of all sensing coil outputs caused by that flaw.

One object of the invention is an electronic scanning method and system for eddy current flaw inspection exhibiting enhanced sensitivity to flaw presence and immunity to spurious noise. These and other objects, advantages and features of the invention will be understood when a detailed description of a preferred embodiment of the invention is described in conjunction with the accompanying drawings.

BEST MODE FOR CARRYING OUT THE INVENTION

Figure 1:
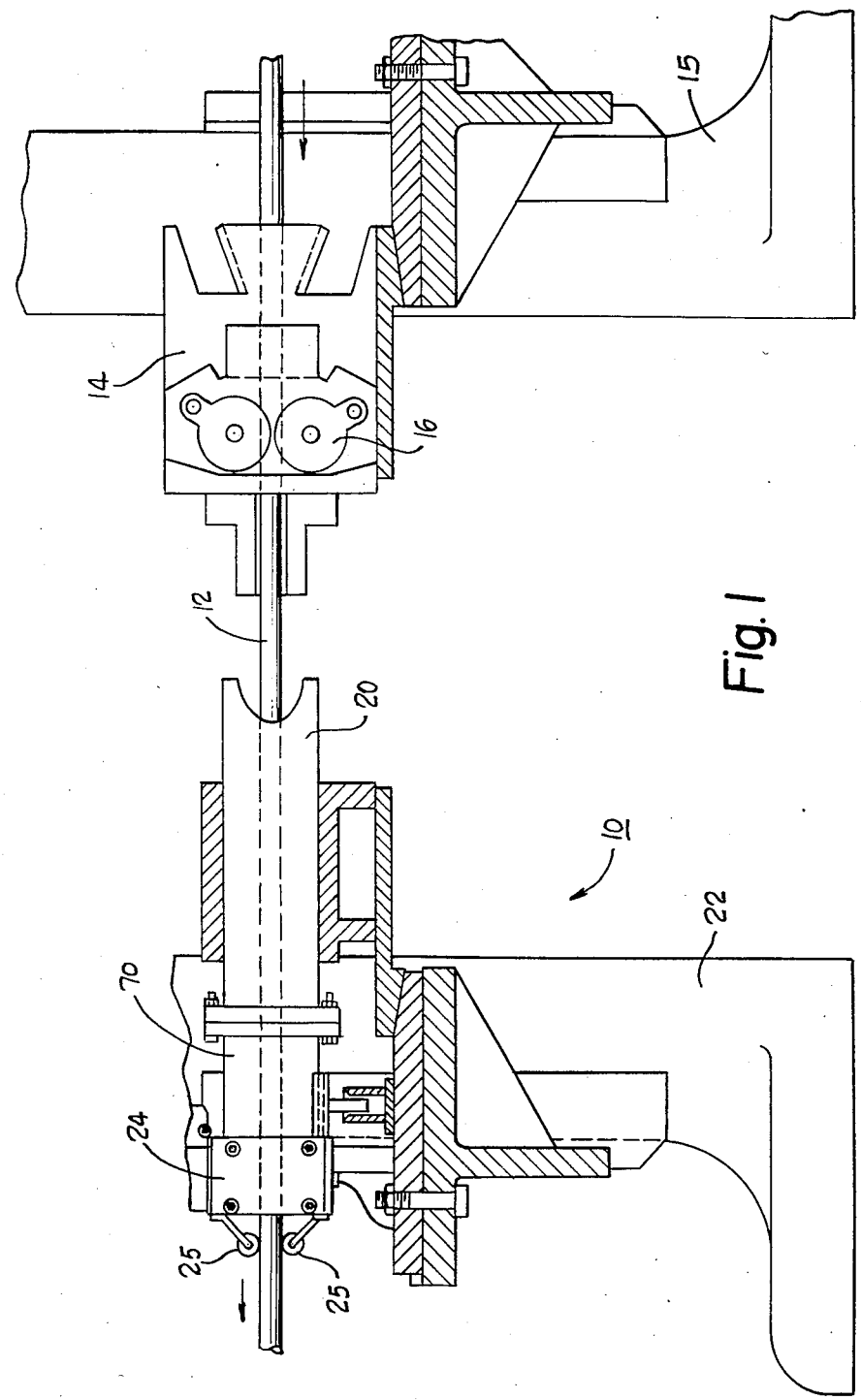
FIG. 1 is a schematic of a workpiece scanning station for electronically searching for flaws in a workpiece including structure for moving the workpiece along a scanning path of travel.

Turning now to the drawings, and in particular FIG. 1, there is illustrated a workpiece inspection station 10 located downstream from a shaping station which shapes a workpiece 12 as it moves along a path of travel to the inspection station. A shaping station exit guide 14 is fixed to and supported by a stand 15. The exit guide 14 includes guide rollers 16 that direct the workpiece 12 to the inspection station 10.

The workpiece 12 defines a generally cylindrical outer surface. An entrance guide 20 is fixed to and supported by a second stand 22 and directs the workpiece through the inspection station 10. The temperature of the workpiece may be at room temperature or may be at an elevated temperature needed to shape the workpiece into a cylinder. In the illustrated embodiment, the inspection station 10 inspects hot workpieces just after shaping. A test head 24 circumscribes the workpiece travel path and positions excitation and scanning circuitry in a proper orientation for electronically sensing the presence of flaws on the workpiece surface. Subsequent to the scanning station 10 the workpiece is guided from the test head 24 by exit rolls 25 to marking and/or classifying apparatus (not shown) downstream from the inspection station 10.

Figures 2, 5:
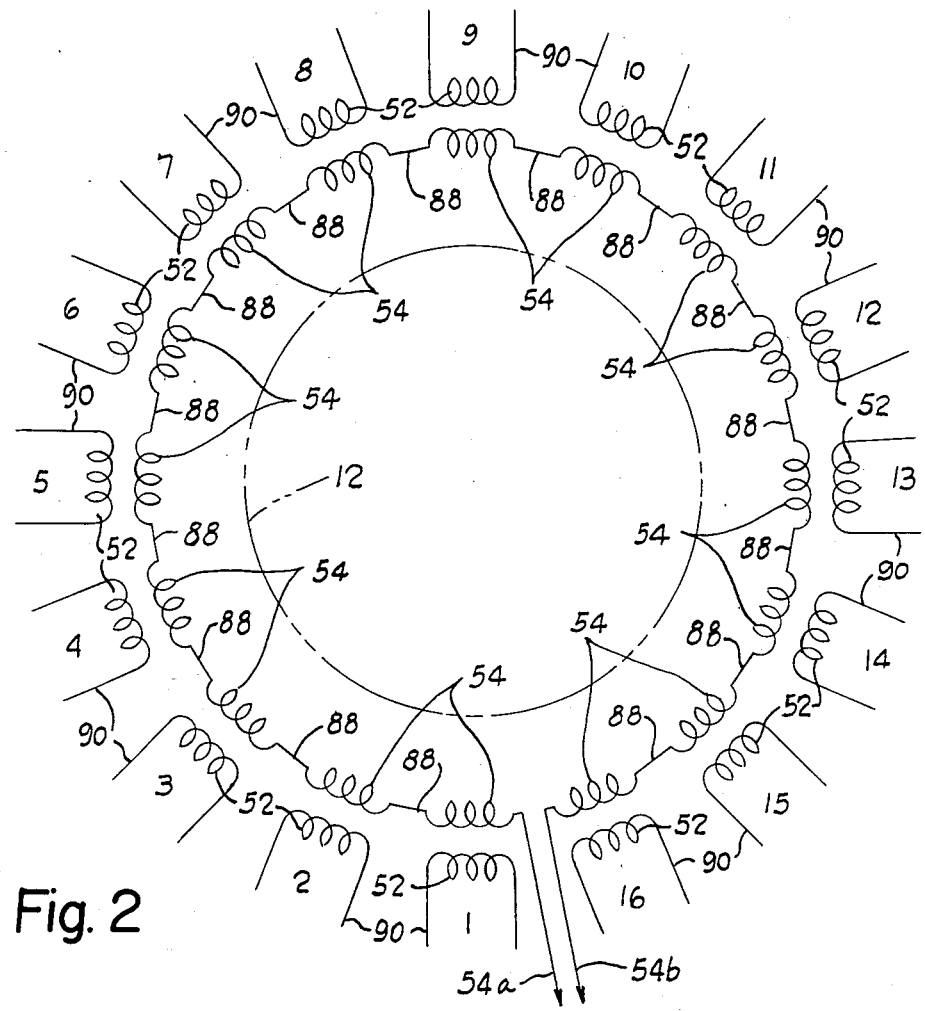
FIG. 2 is a schematic showing a plurality of eddy current inducing and sensing coils positioned in relation to workpiece travel path.
FIG. 5 is a side elevation view of a coil support.
Figure 8:
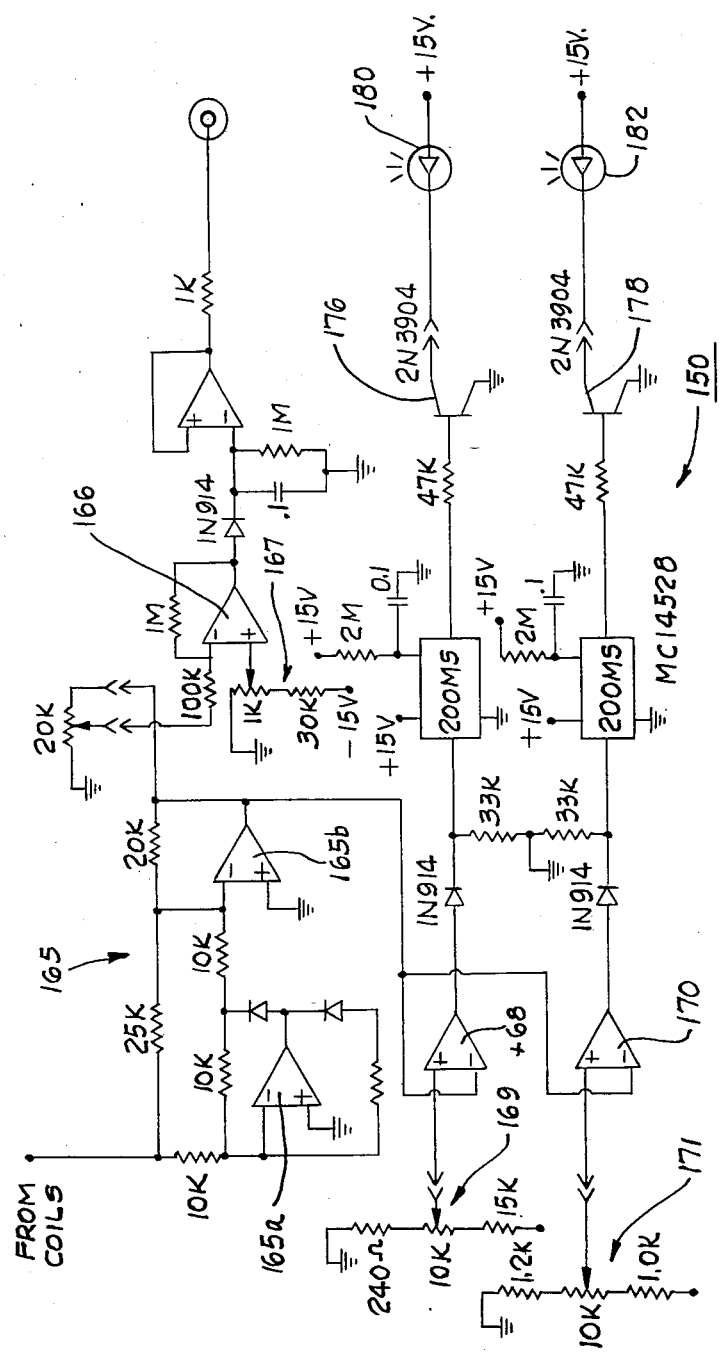
FIG. 8 is a schematic of a circuit for analyzing flaw signal outputs from the sensing coils.

Turning to FIG. 2, the test head 24 supports sixteen transmitting 52 and sixteen sensing 54 coils equally spaced about and radially outward from a workpiece travel path. The transmitting coils 52 (designated with coil numbers 1–16) are coupled to excitation circuitry (FIGS. 3 and 4) that energizes the coils 52 to create a magnetic field that scans about the circumference of the workpiece. The sensing coils 54 are series connected to two outputs conductors 54a, 54b leading to analyzing circuitry (FIG. 8) for determining flaw position and severity. Each of the transmitting coils 52 is individually energizable and in accordance with a preferred method, two adjacent coils are energized simultaneously.

The transmitting and sensing coils 52, 54 are arranged in pairs with each set of two coils sharing a common center axis perpendicular to the workpiece surface. Apparatus for supporting the scanning and transmitting coils 52, 54 within the test head 24 is illustrated in FIGS. 5, 6A, 6B and 7. A coil support 70 defines a through passage 72 for receipt of the workpiece in its travel path from the workpiece shaping station. The coil support 70 includes a cylindrical arm 70a defining a series of radial openings 74 located at spaced locations about the support arm 70a. Sixteen openings are needed to accommodate sixteen sets of sensing and transmitting coils 52, 54. The openings 74 are offset into two sets of eight openings each. The angular separation between the center of adjacent openings 74 in a given set is 45° (FIG. 7) so that the eight openings 74 circumscribe the entire 360° of the cylindrical portion.

Figure 6A:
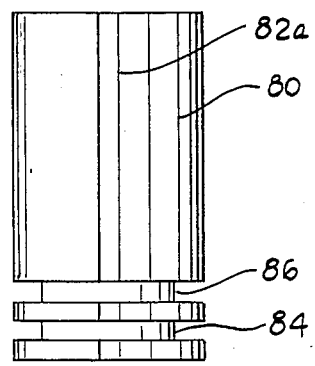
FIGS. 6A and 6B are side and end elevation views of a coil bobbin for mounting coils to the FIG. 5 support.
Figure 6B:
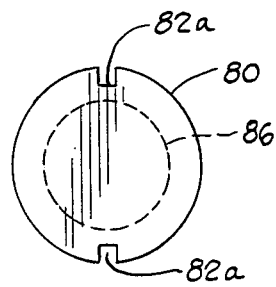
Figure 7:
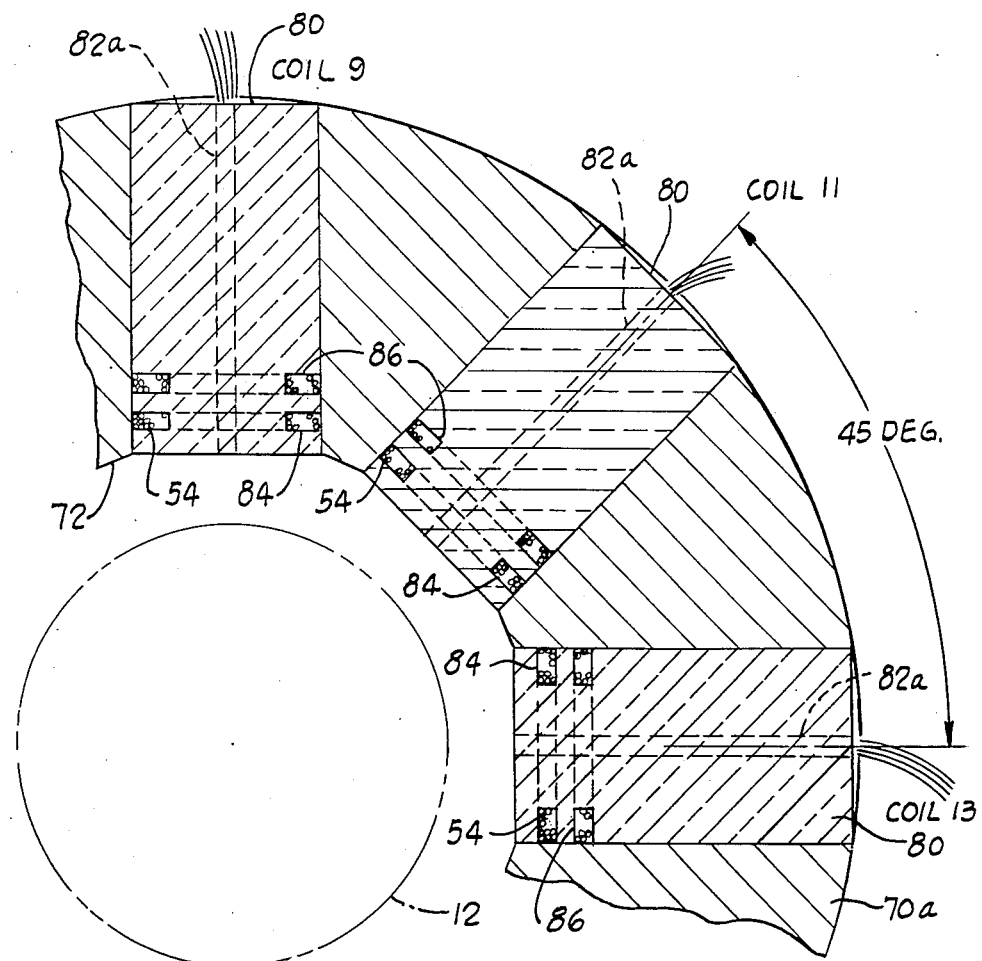
FIG. 7 is a section view of a portion of the FIG. 5 coil support with two coil bobbins shown positioned for scanning of a workpiece.

Each pair of sensing and transmitting coils is supported within one of the coil apertures 74 on a cylindrical coil bobbin 80 (FIGS. 6A, 6B). Each bobbin 80 is constructed from a ceramic insulating material and includes slots 82a, 82b extending on opposite sides along the length of the bobbin to accommodate conductors routed through the slots 82a, 82b to conducting coils wound in two grooves 84, 86 near one end of each bobbin. An inner most groove 84 locates a sensing coil 54 and an outer groove 86 locates a transmitting coil 52. Conductors 88 (FIG. 2) interconnecting the sensing coils 54 are routed along one slot 82a to the outside surface of the support arm 70a to series couple the sensing coils 54. Energization conductors 90 for the transmitting coils 52 are routed through an opposite slot 82b to transmitting circuitry for selectively energizing the coils 52.

Adjacent sensing coils (coils 1 and 2 for example) are differentially wound. A flaw beneath one coil generates an output of one sense from one coil and will produce an output of an opposite sense from a neighboring sensing coil. Since two adjacent sensing coils are near each other but offset circumferentially, a flaw will encounter one sensing coil at a time. Workpiece wobble experienced as the workpiece moves along its travel path will, however, affect both sensing coils nearly equally. The differential winding results in cancellation of eddy current signals caused by the wobble but not signals induced by flaws in the workpiece.

Figure 3:
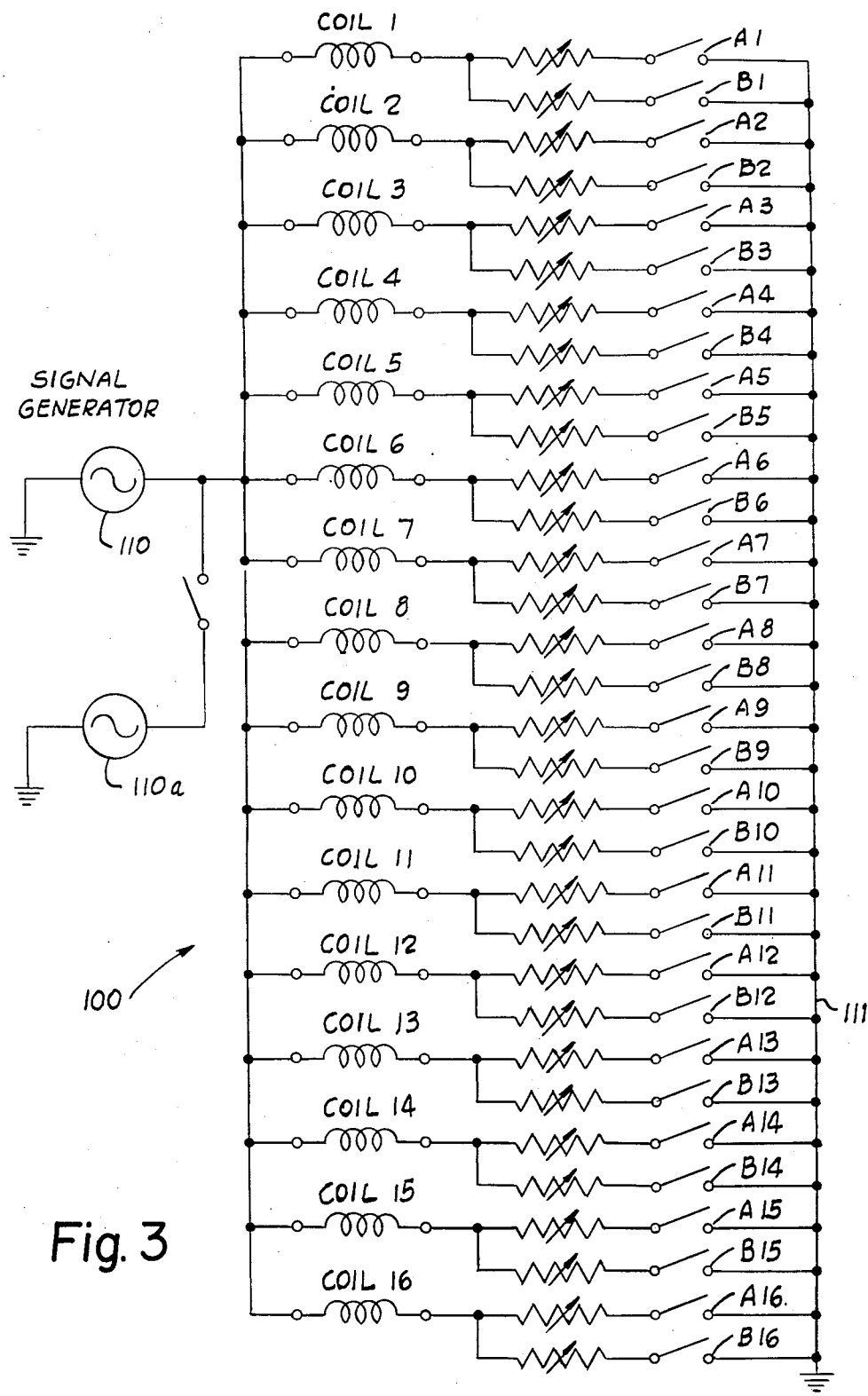
FIGS. 3 and 4 are schematics of circuits to energize eddy current inducing coils.

Turning now to FIG. 3, switching circuitry 100 for energizing the transmitting coils 52 is shown schematically coupled across the sixteen coils. A signal generator 110 produces a sinusoidal output of variable frequency. The transmitting and sensing coils 52, 54 send and receive high frequency signals (approximately 500 khz) that have proven effective in scanning for shallow flaws at the workpiece surface. The signal generator 110 is coupled to each of the transmitting coils 52 so that whenever a ground connection 111 (FIG. 3) to a given coil is completed by the switching circuit 100, the coil is energized with a high frequency signal from the generator 110 to induce eddy currents at the workpiece surface.

To controllably ground and thereby energize a given coil, the coils are connected to two analog switches including switch contacts A1–A16, B1–B16 (FIG. 4) which are sequentially closed in a controlled sequence so that the magnetic field created by coil energization scans sequentially about the workpiece 14 at a desired rate to approximate the scanning accomplished with the mechanical scanning of the prior art.

Figure 4:
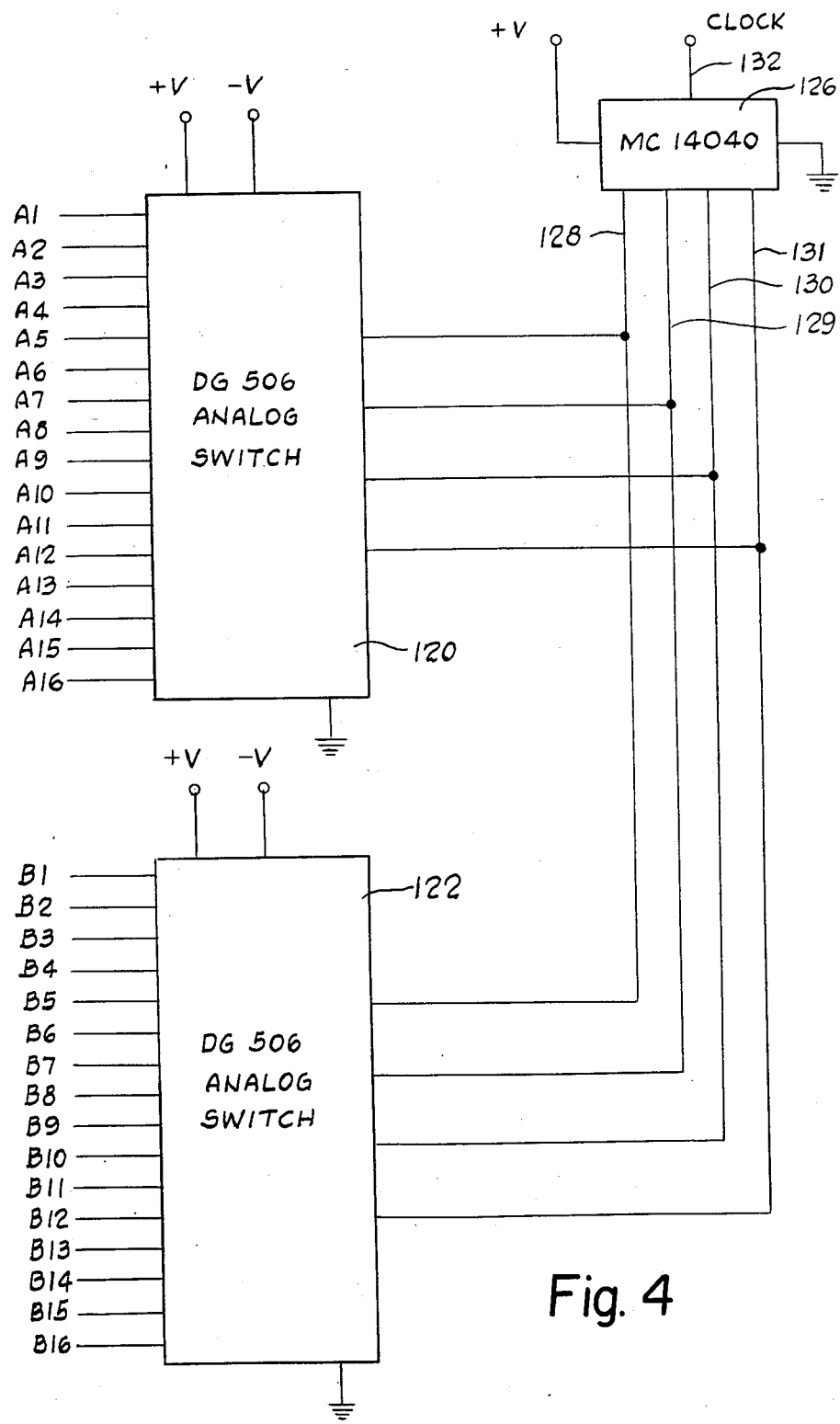

The switch contacts are contained in two integrated circuits 120, 122 coupled to a controllor 126 (FIG. 4). Each of the integrated circuits 120, 122 includes 16 switch contacts that are selectively closed depending upon the status of four control outputs 128, 129, 130, 131 from the controller 126.

The controllor 126 includes a clock input 132 running at a control frequency that causes the controllor 126 to output a four bit control signal on the outputs 128–131. The controller 126 operates as a counter that counts to sixteen and then recycles. Each of the sixteen status conditions results in the closure of two switch contacts. When all four outputs are low (approxmately zero volts), switch contacts A1 and B2 coupled to adjacent transmitter coils Coil 1 and Coil 2 are closed. The next clock cycle takes one control output 128 high. This state causes switch contacts A2 and B3 to close. As seen in FIG. 3, when A1 and B2 are closed, coils 1 and 2 are energized. When contacts A2 and B3 are closed, coils 2 and 3 are energized. Each clock signal causes a change in the coil energization status to cause the resulting magnetic field created by coil energization to rotate around the workpiece.

The controller 126 cycles through the sixteen states until it reaches the control output configuration that closes the two contacts A16, B1 to energize coils 16 and 1. The next clock signal returns the controller to the state with all outputs low so that contacts A1, B1, are again closed to energize coils 1 and 2.

If the clock input has a frequency of N the magnetic field caused by the generator 110 circles the workpiece with a frequency of N divided by 16. This frequency can be adjusted by adjusting the clock frequency at the clock input 132.

As an alternative to using a single variable frequency signal generator 110 a second generator 110a with a different frequency than the first can be connected to the coils 52 through a switching circuit. By simultaneously connecting both generators 110, 110a to the coils 52, multiple frequency excitation is achieved. This can cancel spurious signal response at the sensing coils 54 caused by variations in winding of the transmitting coils 52.

A detection circuit 150 (FIG. 8) receives an output signal from the series connected sensing coils 54, that has been filtered by a bandpass filter that rectifies that signal, and transmits it to a number of comparators which classify the defects as to severity and depth. The filtered output is coupled to a precision rectifier 165 that utilizes two operational amplifiers 165a, 165b to rectify and filter the sensing coil output. This signal is then coupled to three comparator amplifiers 166, 168, 170.

A reference input on each of these comparators can be controlled by adjusting variable potentiometers 167, 169, 171 connected to these reference inputs. Based upon the magnitude of the output from the coils 54, the comparators, 166, 168, 170 produce either a low or high output.

In a preferred embodiment of the invention, an output 174 from the amplifier 166 is coupled to a recorder for generating a permanent record of the output from the coils. The output from the comparators 168, 170 selectively turns on two transistors 176, 178 which in turn activate two visual indicators 180, 182. In combination a first comparator 168 and indicator 180 act as a shallow seam or flaw detector and a second comparator 170 and indicator 182 act as a deep seam or flaw detector. It should be appreciated that an audible alarm can also be generated based upon a comparison between the output from the coils 54 and a reference level.

In operation, as the workpiece 12 passes through the test head 24 the coils 52 are sequentially energized at a rate to cause scanning of the resultant magnetic field around the workpiece. The sensing coils 54 monitor induced eddy currents at the workpiece surface. By coordinating the coil excitation rate with the detecting circuit 150 both the circumferential location and depth of a flaw is determined. The magnitude of the signals at the three comparators 166, 168, 170 classifies and records the flaw severity so that corrective steps can be taken to reduce flaw incidence.

The present invention has been described with a degree of particularity. It is the intent that the invention include all modifications and alterations from the disclosed design falling within the spirit or scope of the appended claims.

We claim:

1. An eddy current flaw inspection system comprising:
   drive means for propelling an elongated workpiece along a workpiece path;
   a pluraltiy of individually energizable transmitter coils distributed at generally equally spaced locations in an encircling arc about the workpiece path with each of said plurality of coils oriented about a center coil axis that intersects an outer workpiece surface;
   a signal generator for providing a coil energization signal;
   excitation circuitry including
   (i) switching means coupled to the signal generator for simultaneously coupling the energization signal to a pair of adjacent transmitter coils to induce eddy currents in the workpiece radially inward of said pair of transmitter coils; and
   (ii) control means for causing the switching means to sequentially connect the signal generator to selected different coil pairs, causing said eddy currents to scan circumferentially around the workpiece;

a plurality of generally equally spaced series coupled sensing coils spaced around the workpiece for sensing induced eddy currents in the workpiece during the transmitter coil energization to detect flaws in the workpiece; and structure for mounting said plurality of sensing coils and transmitter coils in one to one relation to form a plurality of transmitter/sensing coil sets sharing a common coil axis.

2. The system of claim 1, further comprising:
(a) filter circuitry coupled to said sensing coils for separating detected electrical signals in different frequency ranges; and
(b) comparision circuitry coupled to said filtration circuitry for providing a signal which is a function of the signals in the sensing coils.

3. The system of claim 1 wherein one transmitter coil and one sensing coil are supported by a coil mounting bobbin with a plurality of mounting bobbins spaced about the workpiece travel path.

4. The flaw inspection system of claim 1 wherein adjacent sensing coils are differentially wound about an axis that intersects the workpiece.

5. A method for eddy current flaw inspection of a workpiece comprising the steps of:
(a) propelling a workpiece to be inspected along a workpiece path;
(b) positioning a plurality of generally equally spaced, multiple turn transmitter coils in a circular array around the workpiece with each coil having a center axis that intersects the workpiece surface;
(c) simulating rotary scanning of the workpiece as it moves along the workpiece path by sequentially directing electromagnetic energy to the workpiece surface from a sequence of different locations by energizing first and second transmitter coils to form a first energized coil pair, de-energizing a first coil of said first and second transmitter coils while energizing a third transmitter coil adjacent said second transmitter coil to form a subsequent energized coil pair including the second and third transmitter coils and sequentially energizing and de-energizing coils in the array to cause the pairs of energized coils to induce eddy currents in a circular arc that travels around the workpiece at a controlled rate;
(d) positioned a plurality of generally equally spaced series coupled detection coils next to the workpiece path with each detection coil having a center axis oriented perpendicular to the workpiece surface;
(e) detecting eddy currents induced in said workpiece by the electromagnetic energy from the transmitter coils by monitoring induced signals in the detection coils; and
(f) producing flaw indicating signals in response to the detection of said induced eddy currents.

6. Eddy current flaw detection apparatus comprising:
(a) drive means for propelling an elongated workpiece having a cylindrical outer surface along a workpiece travel path;
(b) a variable frequency signal source for setting up eddy currents in the workpiece;
(c) an array of individually energizable exciter coils spaced around the workpiece path, each exciter coil of said array having a center axis oriented to intersect an outer workpiece surface;
(d) an array of series coupled sensing coils, each sensing coil sharing a common center axis with one of said exciter coils to form a exciter/sensor coil set;
(e) sensing circuitry coupled to the series coupled sensing coils to monitor output signals from said sensing coils created by the eddy currents and correlating those signals to flaw locations; and
(f) switching means to selectively energize one or more of the individually energizable exciter coils in a controlled sequence by coupling said signal source to said one or more exciter oils and
(g) coil mounting structure comprising a cylindrical coil form having radially inward openings facing the workpiece travel path and a plurality of generally cylindrical coil bobbins positioned within the coil form openings to locate the coil sets about the travel path, where each coil bobbin has two circular grooves to support one sensing and one exciter coil relative the travel path.

7. An eddy current flaw inspection system comprising:

drive means for propelling an elongated workpiece along a workpiece path;

an array of tansmitter coils distributed in a circular arc aobut the workpiece path wherein each transmitter coil of the array is wound about a coil axis that is oriented generally radially inward toward the workpiece path;

a signal generator for providing a transmitter coil energization signal;

excitation circuitry for individually coupling the transmitter coils to the signal generator in a timed sequence along said circular arc to induce eddy currents in a workpiece passing through said circular arc;

multiple, series connected, substantially circular detection coils spaced around said workpiece path having coil axes in common with the array of transmitter coils, wherein adjacent detection coils are differentially wound to cause signals induced by irregular workpiece movement to cancel; and, monitoring circuitry coupled to said multiple series connected detection coils to monitor induced signals in the detection coils and correlate the induced signals with flaws in the elongated workpiece.

* * * * *